United States Patent
Komatsu et al.

(10) Patent No.: US 9,632,092 B2
(45) Date of Patent: Apr. 25, 2017

(54) REAGENT FOR DIAGNOSING TUMOR, PHARMACEUTICAL COMPOSITION, AND SCREENING METHOD

(71) Applicant: Tokyo Metropolitan Institute of Medical Science, Tokyo (JP)

(72) Inventors: Masaaki Komatsu, Tokyo (JP); Yoshinobu Ichimura, Tokyo (JP)

(73) Assignee: Tokyo Metropolitan Institute of Medical Science, Tokyo (JP)

( * ) Notice: Subject to any disclaimer, the term of this patent is extended or adjusted under 35 U.S.C. 154(b) by 0 days.

(21) Appl. No.: 14/795,009

(22) Filed: Jul. 9, 2015

(65) Prior Publication Data

US 2016/0003834 A1 Jan. 7, 2016

Related U.S. Application Data

(62) Division of application No. 13/910,544, filed on Jun. 5, 2013, now Pat. No. 9,090,681.

(30) Foreign Application Priority Data

Dec. 12, 2012 (JP) ................................. 2012-271249

(51) Int. Cl.
*G01N 33/574* (2006.01)
*C07K 16/18* (2006.01)
*C07K 16/44* (2006.01)
*C07K 14/47* (2006.01)
*C12Q 1/48* (2006.01)
*G01N 33/68* (2006.01)

(52) U.S. Cl.
CPC ....... *G01N 33/57438* (2013.01); *C07K 14/47* (2013.01); *C07K 16/18* (2013.01); *C07K 16/44* (2013.01); *C12Q 1/485* (2013.01); *G01N 33/57496* (2013.01); *G01N 33/68* (2013.01); *C07K 2317/34* (2013.01); *G01N 2333/4703* (2013.01); *G01N 2440/14* (2013.01); *G01N 2500/02* (2013.01)

(58) Field of Classification Search
None
See application file for complete search history.

(56) References Cited

U.S. PATENT DOCUMENTS

2011/0104820 A1 5/2011 Rush et al.

FOREIGN PATENT DOCUMENTS

WO WO 2011/083637 7/2011

OTHER PUBLICATIONS

Komatsu et al., "The selective autophagy substrate p62 activates the stress responsive transcription factor Nrf2 through inactivation of Keap1," *Nature Cell Biology*, 2010; 12(3): 213-224.
Inami et al., "Persistent activation of Nrf2 through p62 in hepatocellular carcinoma cells," *J. Cell Biol.*, 2011; 193(2):275-284.
Jain et al., "*p62/SQSTM1* Is a Target Gene for Transcription Factor NRF2 and Creates a Positive Feedback Loop by Inducing Antioxidant Response Element-driven Gene Transcription," *Journal of Biological Chemistry*, 2010; 285(29): 22576-22591.
Taguchi et al., "Keap1 degradation by autophagy for the maintenance of redox homeostasis," *PNAS*, 2012; 109(34): 13561-13566.
Hancock, Rowena, et al. "Peptide inhibitors of the Keap1—Nrf2 protein—protein interaction." Free Radical Biology and Medicine 52.2 (2012): 444-451.

*Primary Examiner* — Brad Duffy
*Assistant Examiner* — Nelson B Moseley, II
(74) *Attorney, Agent, or Firm* — Barnes & Thornburg LLP

(57) ABSTRACT

The present invention provides antibodies useful for diagnosing and treating tumors as well as methods of screening for antitumor agents. More specifically, tumors can be diagnosed and treated using an anti-phosphorylated p62 antibody that recognizes phosphorylation of serine at position 351 of an amino acid sequence of SEQ ID No. 1 or at a position corresponding thereto. An antitumor agent can be obtained by screening for a substance that inhibits the phosphorylation or that dephosphorylates the phosphorylated serine.

12 Claims, 7 Drawing Sheets

```
Mus musculus      334 SGGDDDWTH SSKEVDPSTGELQSL OMPESEGPSSLDPSQEG 375
Rattus norvegicus 331 SGGDDDWTH SSKEVDPSTGELQSL OMPESEGPSSLDPSQEG 372
Homo sapiens      332 SGGDDDWTH SSKEVDPSTGELQSL OMPESEGPSSLDPSQEG 373
Pongo pygmaeus    332 SGGDDDWTH SSKEVDPSTGELQSL OMPESEGPSSLDPSQEG 373
Bos taurus        332 SGGDDDWTH SSKEVDPSTGELQSL OMPESEGPSSLDPSQEG 373
Xenopus tropicalis 338 SGGDDDWTHVSSKEVDPSTGELQSL QLMETGQPCSLDPTRSS 379
Xenopus laevis    340 AVGDDDWTHVSSKEVDPSTGELQSL QLIETGQPCSLDPNRSS 381
Puffer            315 S--DEEWTH SPKEVDPSTGELQSL QNQ--GLP------SG 345
Danio rerio       243 S--DEEWTH SAKEVDPSTGELQSL RLEQDGADLPAPLNTAS 282
                                    KIR
```

FIG. 1

REAGENT FOR DIAGNOSING TUMOR, PHARMACEUTICAL COMPOSITION, AND SCREENING METHOD

CROSS REFERENCE TO RELATED APPLICATION

This application is a divisional application of U.S. application Ser. No. 13/910,544, which claims the benefit of Japanese Patent Application No. 2012-271249 filed on Dec. 12, 2012, the entire disclosure of both of which are hereby incorporated by reference.

TECHNICAL FIELD

The present invention relates to tumor diagnosis agents, pharmaceutical compositions and screening methods.

BACKGROUND

Nrf2 (nuclear factor erythroid 2-related factor 2) is a transcription factor involved in protecting cells from stresses. Under unstressed conditions, Nrf2 is bound to Keap1 (Kelch-like ECH-associated protein 1) that is an adaptor protein for ubiquitin E3 ligase and is constitutively degraded through the ubiquitin-proteasome pathway. Exposure to certain stresses, however, causes the modification of Keap1, which inhibits its binding to Nrf2. As a result, Nrf2 is accumulated in the nucleus and activates the expression of antioxidant proteins and detoxification enzymes to provide a defense mechanism. Mutations in either Nrf2 or Keap1 have been identified inpatients with, for example, some kind of lung cancer. These mutations cause loss of interaction between Keap1 and Nrf2, which makes tumor cells resistant to anticancer agents (Komatsu M. et al., Nat. Cell Biol. 2010, vol. 12, p. 213-23).

On the other hand, p62 is known as an adaptor molecule which is involved in selective autophagy. p62 can interact with the domain (aa309-624) of Keap1, containing the Nrf2-binding site. Thus, due to the p62 accumulation in cells by a deficiency in autophagy or an overexpression of p62, the binding between Keap1 and Nrf2 is competitively inhibited, resulting in the activation of the aforementioned defense mechanism by free Nrf2 (WO 2011/083637; Komatsu M. et al., Nat. Cell Biol. 2010, vol. 12, p. 213-23).

Aberrant accumulation of p62 has been observed in malignant tumors such as liver cancer or glioma. It has been suggested that increase in Keap1-p62 complex is advantageous for proliferation of malignant liver cancers. This means that the inhibition of their binding can be a target of cancer treatment.

SUMMARY OF THE INVENTION

The present invention is directed to provide antibodies useful for diagnosing and treating tumors as well as methods of screening for antitumor agents.

The Keap1-binding region (aa346-359) (hereinafter, referred to as "KIR") in mouse p62 is highly conserved in various species. KIR interacts with Keap1 using an amino acid sequence of STGE (SEQ ID No. 28) thereof. Biochemical analyses, however, have shown that the binding affinity of p62-KIR for Keap1 is significantly lower than that for Nrf2. Binding mechanism between Keap1 and p62 within cells have unrevealed. The present inventors found that phosphorylation of serine at the position 351 of the amino acid sequence of p62 (SEQ ID No. 1) enhances the binding affinity of KIR for the Keap1-DC domain to a level comparable to that of the Nrf2-ETGE for the Keap1-DC domain. The present invention was thus completed.

An embodiment of the present invention is an isolated phosphorylated p62 protein or a part thereof, comprising a phosphorylated serine at position 351 of an amino acid sequence of SEQ ID No. 1 or at a position corresponding thereto.

Another embodiment of the present invention is an anti-phosphorylated p62 antibody or a part thereof recognizing the phosphorylated p62 protein and not recognizing a non-phosphorylated p62 protein that is not phosphorylated at the serine.

Yet another embodiment of the present invention is DNA encoding the antibody or a part thereof described above.

Yet another embodiment of the present invention is an expression vector comprising the aforementioned DNA and being capable of expressing the antibody or a part thereof described above.

Yet another embodiment of the present invention is a cell comprising the aforementioned DNA and expressing the antibody or apart thereof described above.

Yet another embodiment of the present invention is a hybridoma producing the aforementioned antibody.

Yet another embodiment of the present invention is a tumor diagnosis agent comprising the aforementioned anti-phosphorylated p62 antibody. The tumor may be a liver cancer.

Yet another embodiment of the present invention is a pharmaceutical composition comprising the anti-phosphorylated p62 antibody or a part thereof described above, the aforementioned expression vector, or the aforementioned cell. The pharmaceutical composition may be an antitumor agent. A tumor to be treated with the antitumor agent may be a liver cancer.

Yet another embodiment of the present invention is a method of screening for an antitumor agent comprising screening for a substance inhibiting the phosphorylation, in p62, of serine at position 351 of an amino acid sequence of SEQ ID No. 1 or a serine at a position corresponding thereto, or for a substance dephosphorylating the phosphorylated serine.

Yet another embodiment of the present invention is a method of screening for an antitumor agent comprising screening for a substance inhibiting the binding between the aforementioned phosphorylated p62 protein and Keap1.

In both screening methods, a tumor to be treated with the aforementioned antitumor agent may be a liver cancer.

Yet another embodiment of the present invention is an isolated mutant p62 protein or a part thereof, comprising a substitution of glutamic acid or aspartic acid for serine at position 351 of an amino acid sequence of SEQ ID No. 1 or at a position corresponding thereto.

Yet another embodiment of the present invention is an isolated mutant p62 protein or a part thereof, comprising a substitution of glycine or alanine for serine at position 351 of an amino acid sequence of SEQ ID No. 1 or at a position corresponding thereto.

Yet another embodiment of the present invention is DNA encoding the mutant p62 protein or a part thereof described above.

The present invention made it possible to provide antibodies useful for diagnosing and treating tumors as well as methods of screening for antitumor agents.

BRIEF DESCRIPTION OF THE DRAWING

FIG. 1 shows an alignment of Keap1-interacting regions (KIRs) and LC3 recognition sequences (LRSs) of p62 homologs (SEQ ID Nos. 11-19) of various species. Hatched areas show corresponding amino acid sequences, with perfectly conserved residues being highlighted with a black background and partially conserved residues being highlighted with a gray background (from the top, p62 of mouse, rat, human, orangutan, cattle, *Silurana tropicalis, Xenopus laevis*, pufferfish, and zebrafish).

Figure 2:
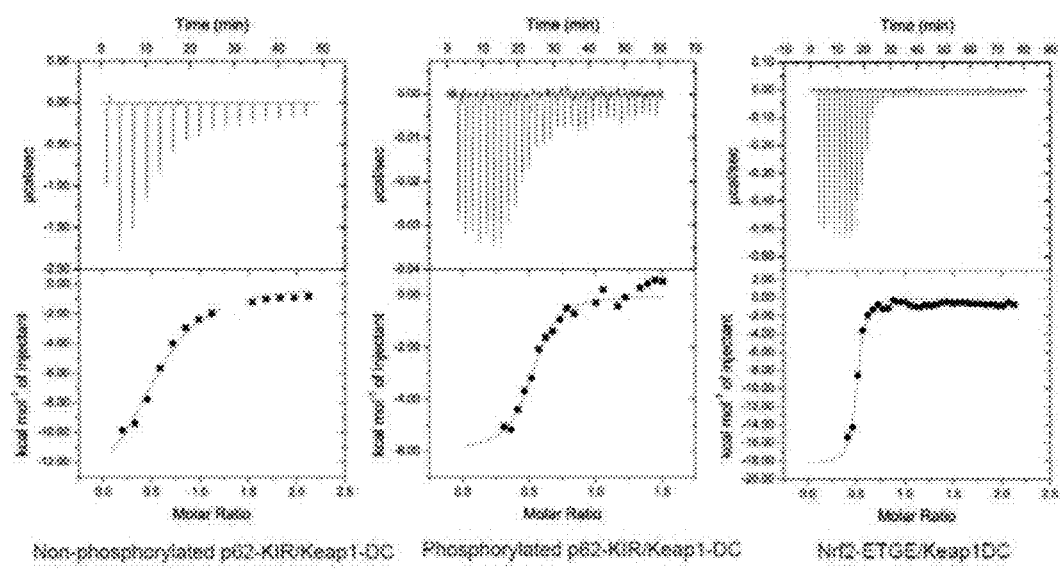

FIG. 2 shows binding isotherms obtained using isothermal titration calorimetry, for the interaction of Keap1-DC (SEQ ID No. 24) with non-phosphorylated p62-KIR (SEQ ID No. 21), phosphorylated p62-KIR (SEQ ID No. 21), or an Nrf2-ETGE motif (SEQ ID No. 26).

Figure 3:
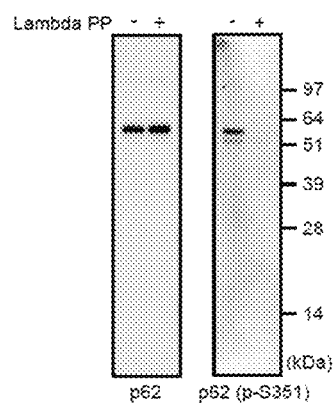

FIG. 3 shows a result of immunoblotting. Strep-tagged p62 was expressed in HEK293T cells, recovered by precipitation with StrepTactin, treated (+) or not treated (−) with lambda protein phosphatase (Lambda PP), and subjected to immunoblotting using anti-p62 antibody or anti-phosphorylated p62 antibody.

Figure 4:
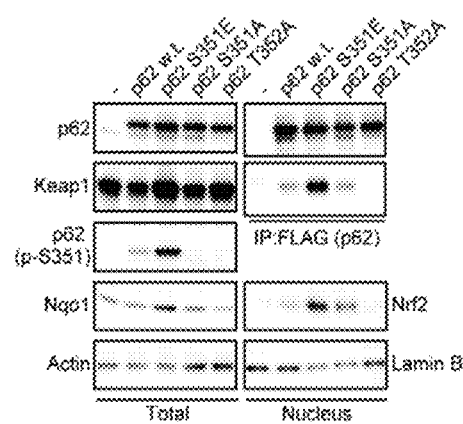

FIG. 4 shows a result of immunoblotting of lysates prepared from normal hepatocytes of a mouse overexpressing FLAG-tagged p62 w.t. (SEQ ID No. 1) (normal p62), S351E (SEQ ID No. 2) (pseudo-phosphorylated p62) obtained by the substitution of glutamic acid for serine 351, S351A (SEQ ID No. 4) (non-phosphorylated p62) obtained by the substitution of alanine for serine 351, and T352A (SEQ ID No. 6) (p62 mutant defective in interacting with Keap1) obtained by the substitution of alanine for threonine 352, using adenovirus infection system.

Figure 5:
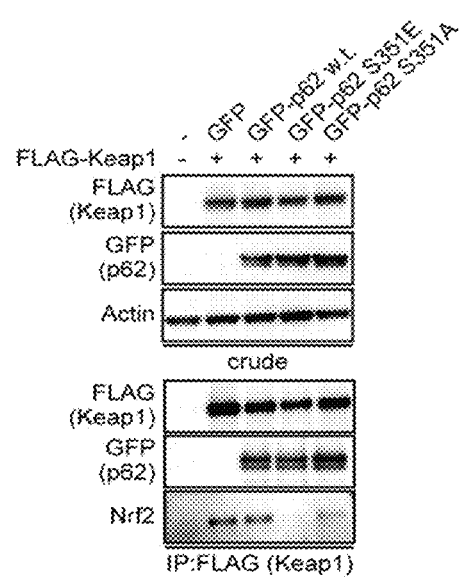

FIG. 5 shows a result of immunoblotting of immunoprecipitates obtained by immunoprecipitating lysates of HEK293T cells coexpressing FLAG-tagged Keap1 (SEQ ID No. 23) and GFP, GFP-p62 S351E (SEQ ID No. 2) or GFP-p62 S351A (SEQ ID No. 4) with an anti-FLAG antibody.

Figure 6:
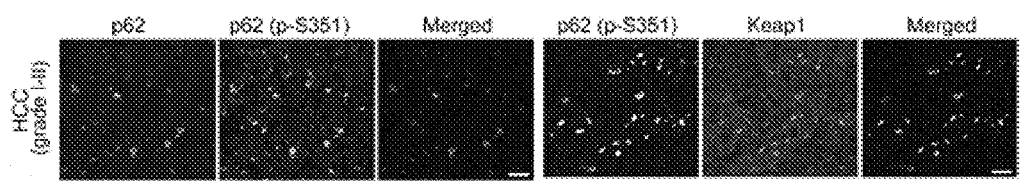

FIG. 6 shows images of HCC immunostained with a combination of anti-p62 antibody and anti-phosphorylated p62 antibody or a combination of anti-phosphorylated p62 antibody and Keap1 (bar: 10 μm).

FIG. 7(*a*) shows photographs of nude mice and tumors removed from the mice, which were taken 50 days after subdermal transplantation of: [Huh-1] parent cell lines, Huh-1_p62$^{-/-}$, or Huh1_p62$^{-/-}$ cells into which wild-type p62 (SEQ ID No. 7) or p62 mutant (p62S349E(SEQ ID No. 8), S349A(SEQ ID No. 9) or T350A(SEQ ID No. 10)) has been introduced, and FIG. 7(*b*) shows the volume (left) and the weight (right) of the tumors 50 days after the transplantation.

MODES FOR CARRYING OUT THE INVENTION

Unless otherwise noted in embodiments and examples, all procedures used are as described in standard protocols such as M. R. Green & J. Sambrook (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., with or without modifications or changes. In addition, unless otherwise noted, a commercial reagent kit or a measurement instrument, if any, is used as described according to protocols attached thereto.

The above and further objects, features, advantages, and ideas of the present invention are apparent to those skilled in the art from consideration of the detailed description of this specification. Furthermore, those skilled in the art can easily reproduce the present invention from these descriptions. The mode(s) and specific example(s) described below represent a preferable embodiment of the present invention, which is given for the purpose of illustration or description. The present invention is not limited thereto. It is obvious to those skilled in the art that various modifications may be made according to the descriptions of the present specification without departing from the spirit and scope of the present invention disclosed herein.

==Phosphorylated p62 Protein==

The present invention is an isolated phosphorylated p62 protein or a part thereof, having a phosphorylated serine at the position 351 of an amino acid sequence of SEQ ID No. 1 or at a position corresponding thereto.

"p62 (or p62 protein)" is known as an ubiquitin-binding protein. Information about the amino acid sequence of p62 or a nucleotide sequence that encodes it is available in public databases. Some accession numbers in these databases are given here. [Database: Accession No. (species)]: NCBI: NP_003891.1 (human), NCBI: NM_003900.4 (human), NCBI: NP_035148.1 (mouse), NCBI: NM_011018.2 (mouse) Swiss-Prot: O08623.1 (rat), NCBI: NP_787037.2 (rat), NCBI: NM_175843.3 (rat), Swiss-Prot: Q5RBA5.1 (orangutan). The term "p62" as used herein include p62 homologs from various animal species (e.g., mammalian species (such as human, monkey, cattle, pig, mouse, and rat), reptile, amphibian, and fish). An amino acid sequence of each of such homologs is at least, for example, 80%, 85%, 90%, or 95% identical to, for example, the amino acid sequence (SEQ ID No. 1) of mouse p62 or has one to some (e.g., two, three, four, five, six, seven, eight, nine, ten, eleven, twelve, thirteen, fourteen, fifteen, sixteen, seventeen, eighteen, nineteen, twenty, or more) deletion(s), substitution(s), insertion(s), or addition(s), compared with the amino acid sequence (SEQ ID No. 1) of mouse p62.

The term "phosphorylated p62 protein" as used herein refers to mouse p62 with an amino acid sequence (SEQ ID No. 1) having a phosphorylated serine at the position 351, or p62 homologs from mammalian species other than mouse (such as human, monkey, cattle, and rat) or other species (such as reptile, amphibian, and fish) with an amino acid sequence having a phosphorylated serine corresponding to serine 351 of mouse p62 (i.e., serine 348 in rat p62, serine 349 in human p62 (SEQ ID No. 7), serine 349 in orangutan p62, serine 349 in cattle p62, serine 355 in *Silurana tropicalis* p62, serine 357 in *Xenopus laevis* p62, serine 332 in pufferfish p62, and serine 260 in zebrafish p62).

The term "part having phosphorylated serine" as used herein refers to part of an isolated p62 having a phosphorylated serine at the position 351 in mouse p62 or at a position corresponding thereto in a p62 from other species. The term "part" in this context may be a peptide made up of two or more amino acids, preferably five or more amino acids, more preferably 10 or more amino acids, and yet more preferably 50 or more amino acids. The part may be a peptide made up of 400 or less amino acids, preferably 300 or less, more preferably, 200 or less, and yet more preferably 100 or less amino acids.

The term "isolated" as used herein means not existing in a living body, but a process to produce an isolated thing is not limited. Therefore it may be isolated from a cell or chemically synthesized as long as it exist outside a living body, is not limited by the method for producing it.

The protein of "a protein or a part thereof" according to the present invention may be a mutant p62 protein (herein referred to as a "pseudo-phosphorylated p62 mutant protein") (e.g., SEQ ID No. 2 or 3 in the case of mouse p62) in which serine 351 for mouse p62 or corresponding serine for p62 from other animal than mouse has been replaced by glutamic acid or aspartic acid and which mimics the phosphorylated p62, or a mutant p62 protein (herein referred to as a "pseudo-non-phosphorylated p62 mutant protein") (e.g., SEQ ID No. 4 or 5 in the case of mouse p62) in which the serine just mentioned has been replaced by alanine or glycine and which mimics the non-phosphorylated p62. In addition, the part thereof of "a protein or a part thereof" according to the present invention may be a part of the mutant p62 protein, which has the mutant amino acid described above.

The aforementioned protein or the part thereof may be chemically synthesized, or alternatively, may be a recombinant protein or recombinant peptide that is expressed in *Escherichia coli* or cultured mammalian cells. Those skilled in the art can produce the recombinant protein or the recombinant peptide using a routine method including in vitro mutagenesis.

The term "Keap1-Interacting Region (KIR)" as used herein refers to a region of p62 which specifically binds to Keap1, that is, a partial amino acid sequence (SEQ ID No. 20) consisting of amino acid residues 346 to 359 of the amino acid sequence of mouse p62 (SEQ ID No. 1) or a region of highly conserved amino acid sequence corresponding to the aforementioned partial amino acid sequence in the amino acid sequence of p62 of mammalian species (such as human, monkey, cattle, and rat) other than mouse or other species (such as reptile, amphibian, and fish) (see FIG. 1).

Information about the amino acid sequence of Keap1 (Kelch-like ECH-associated protein 1) or the nucleotide sequence that encodes it is available in public databases. Some accession numbers in these databases are given here. [Database: Accession No. (species)]: Swiss-Prot: Q14145.2 (human), Swiss-Prot: Q9Z2X8.1 (mouse), GenBank: BAA34639.1 (mouse), GenBank: AB020063.1 (mouse), Swiss-Prot: Q684M4.1 (pig). The term "Keap1" as used herein includes Keap1 homologs from various animal species (e.g., mammalian species (such as human, monkey, cattle, pig, mouse, and rat), reptile, amphibian, and fish). An amino acid sequence of each of such homologs is at least, for example, 80%, 85%, 90%, or 95% identical to, for example, the amino acid sequence (SEQ ID No. 25) of human Keap1 or has one to some (e.g., two, three, four, five, six, seven, eight, nine, ten, eleven, twelve, thirteen, fourteen, fifteen, sixteen, seventeen, eighteen, nineteen, twenty, or more) deletion(s), substitution(s), insertion(s), or addition(s), compared with the amino acid sequence of human Keap1.

==Anti-Phosphorylated p62 Antibody==

The term "anti-phosphorylated p62 antibody" as used herein refers to antibody that recognizes phosphorylated p62 protein having a phosphorylated serine at the position 351 in the case of mouse p62 (SEQ ID No. 1) or at a position corresponding thereto in the case of other species and does not recognize p62 protein that is not phosphorylated (herein referred to as "non-phosphorylated p62 protein") at serine 351 in the case of mouse p62 or at a serine corresponding thereto in the case of other species. This antibody may be referred to as antibody that binds the phosphorylated p62 protein but does not bind the non-phosphorylated p62 protein, or alternatively, antibody that interacts with the phosphorylated p62 protein but does not interact with the non-phosphorylated p62 protein. The animal species from which p62 recognized by the antibody was derived is not specifically limited. It is, however, preferable that p62 is derived from mammal, and more preferable that p62 is mouse, rat or human p62. Species specificity by which the antibody recognizes the antigen is not specifically limited. Various types of specificity can be contemplated including antibody that can distinguish the phosphorylated p62 and the non-phosphorylated p62 only in human p62, antibody that can distinguish the phosphorylated p62 and the non-phosphorylated p62 only in mouse p62, and antibody that can distinguish the phosphorylated p62 and the non-phosphorylated p62 of human and non-human p62 (e.g., antibody that can distinguish the phosphorylated p62 and the non-phosphorylated p62 of human and mouse or antibody that can distinguish the phosphorylated p62 and the non-phosphorylated p62 of human and monkey but not of mouse.

The anti-phosphorylated p62 antibody has a high binding affinity for the phosphorylated p62 protein and has a binding constant (Ka) of preferably at least $10^9$ M$^{-1}$, more preferably at least $10^{10}$ M$^{-1}$, and further more preferably at least $10^{11}$ M$^{-1}$. In addition, the antibody has a low binding affinity for the non-phosphorylated p62 protein and has a binding constant (Ka) of preferably at most $10^4$ M$^{-1}$, more preferably at most $10^3$ M$^{-1}$, and further more preferably at most $10^2$ M$^{-1}$. It is also preferable that the anti-phosphorylated p62 antibody recognizes the pseudo-phosphorylated p62 mutant protein and does not recognize the non-phosphorylated p62 protein.

The antibody may be monoclonal or polyclonal, or may be artificial antibody such as humanized antibody. These kinds of antibody may be produced using a method known to those skilled in the art. Antigen to be used for the production of the antibody may be an isolated phosphorylated p62 protein having a phosphorylated serine at the position 351 of the amino acid sequence of SEQ ID No. 1 or at a position corresponding thereto, or the aforementioned a part having the phosphorylated serine. Other choices include a pseudo-phosphorylated p62 mutant protein in which aspartic acid or glutamic acid has been introduced in place of the phosphorylated serine, or a part thereof having the aspartic acid or glutamic acid. Details of these peptides are as described above. The antibody that does not recognize the non-phosphorylated p62 protein but recognizes the phosphorylated p62 protein can be purified by passing the fraction bound to the column of the phosphorylated p62 protein through a column of the non-phosphorylated p62 protein and collecting the eluted fraction.

The term "part of anti-phosphorylated p62 antibody" as used herein refers to antigen-binding fragments comprising the variable region, such as Fab fragments and F(ab')$_2$ fragments. These fragments may be obtained by, for example, partial digestion of monoclonal antibody with protease. The protease may be any one of suitable proteases as long as it can provide an Fab fragment or an F(ab')$_2$ fragment. Examples of the protease that can be used include pepsin and ficin.

Another embodiment of the present invention may be DNA that encode the anti-phosphorylated p62 antibody or a fragment thereof, or an expression vector comprising such DNA and capable of expressing the anti-phosphorylated p62 antibody or a fragment thereof. The DNA and the expression vector can be produced using a method known to those skilled in the art.

The anti-phosphorylated p62 antibody or a fragment thereof may be produced by making an expression vector using a promoter that functions in *Escherichia coli* or cultured mammalian cells, introducing the expression vector into a host cell to express the antibody or a fragment thereof, and purifying it. It is preferable that a signal peptide is added for secretion out of the host cells.

==Tumor Diagnosis Agent==

Since the binding constants (Ka) of the non-phosphorylated p62-KIR and the Nrf2-ETGE, to Keap1-DC are $(5.67\pm1.19)\times10^4$ $M^{-1}$ and $(6.83\pm2.16)\times10^6$ $M^{-1}$, respectively, as described in Example 1, Keap1 preferentially binds to Nrf2 even in the presence of the non-phosphorylated p62. The binding constant of the phosphorylated p62-KIR to Keap1-DC is, however, $(5.12\pm1.80)\times10^6 M^{-1}$, which is about 100 times higher than that of KIR of the non-phosphorylated p62 and is comparable to the binding constant of Nrf2-ETGE to Keap1-DC. Thus, phosphorylation of p62 allows it to bind to Keap1 even in the presence of Nrf2, increasing the unbound Nrf2. The free Nrf2 enhances the expression of target genes. This advantageously affects the proliferation of malignant cancers.

The number of the free Nrf2 molecule increases with more phosphorylated p62 present in cancer cells. Accordingly, malignant progression of tumors can be diagnosed by the detection or quantitative determination of the phosphorylated p62.

Specifically, the phosphorylated p62 in tumor cells of a patient is quantitatively determined two or more times at given intervals. If the amount of the phosphorylated p62 or its ratio to the total p62 is increased, the tumor can be considered to be more malignant than before, and if decreased, the tumor can be considered to be benignant than before. This method can also be used to determine the efficacy of an anticancer agent. Specifically, the phosphorylated p62 in tumor cells of a patient is quantitatively determined before and after the administration of an anticancer agent. If the amount of the phosphorylated p62 or its ratio to the total p62 is increased, the anticancer agent can be considered to be ineffective to that tumor, and if decreased, the tumor can be considered to be effective to that tumor. Based on this efficacy, an antitumor agent to be used can be selected. Target genes of Nrf2 include multidrug efflux transporter genes. Some lung cancer cells are known to be resistant to antitumor agents through the activation of Nrf2. This suggests that the antitumor agents selected on the basis of their capacity to reduce the phosphorylated p62 are less susceptible to drug resistance.

How to detect the phosphorylated p62 is not specifically limited, but it is preferable to use an assay using antibody, i.e., an immunoassay, such as immunoblotting, ELISA and immunohistochemical staining.

Thus, the anti-phosphorylated p62 antibody is useful as a tumor diagnosis agent because it can easily detect or quantitatively determine the phosphorylated p62.

==Pharmaceutical Composition==

Pharmaceutical compositions according to the present invention comprise the anti-phosphorylated p62 antibody or a part thereof, the expression vector having a DNA that encodes the anti-phosphorylated p62 antibody or a part thereof and being capable of expressing the anti-phosphorylated p62 antibody or a part thereof, and cells having DNA that encodes the anti-phosphorylated p62 antibody or apart thereof and expressing the anti-phosphorylated p62 antibody or a part thereof. The pharmaceutical compositions may be used as an antitumor agent. The anti-phosphorylated p62 antibody or a part thereof is preferably an inhibitory antibody that inhibits the binding of the phosphorylated p62 protein to Keap1, and in particular, is preferably an inhibitory antibody that inhibits the binding of the phosphorylated p62 protein to a region of the Keap1-DC domain (e.g., a region of aa309-624 (SEQ ID No. 27) or aa321-609 (SEQ ID No. 24)).

The subject to which the pharmaceutical composition is to be administered is not limited as long as it is vertebrate, but is preferably human. For example, it is expected to suppress proliferation of tumor cells by administering the pharmaceutical composition of the present invention to a patient with the tumor. Tumors to be treated with the antitumor agent are not specifically limited and any tumors that have become malignant due to the phosphorylation of p62 are applicable. It is, however, preferable that the tumor to be treated is liver cancer.

The pharmaceutical composition may be formulated into a tablet, powder, granules, particulates, a capsule, liquid, emulsion or suspension with the addition, if necessary, of a pharmaceutically acceptable carrier to form an antitumor agent. The pharmaceutically acceptable carrier as used herein may appropriately be selected from ordinary carriers depending on the form of medicament to be prepared. For example, when the medicament is prepared as a solution, examples of the carrier that can be used include purified water (sterile water) or physiological buffer, or injectable organic esters such as glycol, glycerol, and olive oil. The medicament may comprise an stabilizer, an excipient, or other agent that is ordinarily used. A mode of administration of the medicament is not specifically limited and may appropriately be determined depending on, for example, dosage form, age, sex, and other factor(s) of the patient, and severity of the disease. The dosage form is preferably parenteral one such as injections, infusions, and aerosols. When the medicament is used as an injection or infusion, it is mixed with, when necessary, salt solution or ordinary therapeutic fluid such as glucose or amino acid, and administered intravenously, intramuscularly, intradermally, subcutaneously, or intraperitoneally. The medicament may be used alone or in combination with other agent (such as other antitumor agent or an agent that alleviates the condition.

==Screening for Antitumor Agent==

Screening for the antitumor agent of the present invention against the p62 protein can be performed by evaluating whether a candidate substance inhibits the phosphorylation of serine at the position 351 of the amino acid sequence of SEQ ID No. 1, or at a position corresponding thereto, or whether the candidate substance can dephosphorylate the phosphorylated serine. Alternatively, the screening can be performed by evaluating whether a candidate substance inhibits the binding of the phosphorylated p62 protein to Keap1. As will be shown in the Examples below, these substances are effective to inhibit proliferation of tumor cells. Thus, with the screening according to the present invention, it is possible to effectively obtain an antitumor agent. Tumors to be treated with the antitumor agent are not specifically limited and any tumors that have become malignant due to the phosphorylation of p62 are applicable. It is, however, preferable that the tumor to be treated is liver cancer. The candidate substance is not specifically limited and may be a high molecular weight molecule or a protein such as antibody, or a low molecular weight molecule such as a chemical compound.

The specific procedure of the screening to be used can appropriately be designed by those skilled in the art. For example, a candidate substance may be added to cultured mouse cells comprising the phosphorylated p62 having a phosphorylated serine at the position 351 of the amino acid sequence of SEQ ID No. 1, and the amount of the phosphorylated p62 may be measured before and after the administration. If the amount after the administration is lower than that before the administration, the compound can be considered as a potential antitumor agent. The amount of the phosphorylated p62 protein can be quantitatively determined by, for example, immunoblotting using the anti-phosphorylated p62 antibody that recognizes the phosphorylated p62 protein and does not recognize the non-phosphorylated p62 protein in which the serine in question has not been phosphorylated.

EXAMPLES

The present invention is described more specifically with reference to the Examples below. The scope of the present invention, however, is not limited to the following Examples.

Example 1

This Example shows that phosphorylation of p62 increases its binding affinity for Keap1.
(1) In-Vitro Binding Affinity of Phosphorylated p62 for Keap1

Binding isotherms were obtained using isothermal titration calorimetry, for the interaction of mouse Keap1-DC (aa321-609, SEQ ID No. 24) with KIR in mouse non-phosphorylated p62 (SEQ ID No. 21), KIR in mouse phosphorylated p62 (SEQ ID No. 21), or an ETGE motif of mouse Nrf2 (SEQ ID No. 26) (FIG. 2).

First, isothermal titration calorimetry was performed using MicroCal iTC$_{200}$ System (GE Healthcare) at 25° C. 2.5 µl of 0.1 mM solution of non-phosphorylated KIR ($^{348}$VDPSTGELQ$^{356}$, SEQ ID No. 21) was injected from a rotating syringe (1000 rpm) into 200 µl of 0.1 mM solution of Keap1-DC sixteen times at an interval of 3 minutes. 1.3 µl of 0.6 mM phosphorylated KIR ($^{348}$VDP(pS)TGELQ$^{356}$) solution was injected from a rotating syringe (1000 rpm) into 200 µl of 0.06 mM Keap1-DC solution thirty times at an interval of 2 minutes. 1 µl of 0.4 mM solution of Nrf2-ETGE motif ($^{76}$LDEETGEFL$^{84}$, SEQ ID No. 26) were injected from a rotating syringe (1000 rpm) into 200 µl of 0.04 mM of Keap1-DC (SEQ ID No. 24) forty times at an interval of 2 minutes. The binding data were analyzed using Origin 7 software (GE healthcare).
==Result==
Binding constants (Ka) of the non-phosphorylated p62-KIR, the phosphorylated p62-KIR, and the Nrf2-ETGE, to Keap1-DC were (5.67±1.19)×10$^4$ M$^{-1}$, (5.12±1.80)×10$^6$ M$^{-1}$, and (6.83±2.16)×10$^6$ M$^{-1}$, respectively.

KIR in the phosphorylated p62 had an approximately 100 times higher binding affinity for Keap1-DC than KIR in the non-phosphorylated p62, which is comparable to the binding affinity of Nrf2-ETGE for Keap1-DC.
(2) Generation of Anti-Phosphorylated p62 Antibody A peptide consisting of the amino acid sequence CKEVDP(pS)TGELQSLQ (SEQ ID No. 22), obtained by phosphorylating serine 351 in the amino acid sequence of SEQ ID No. 1 and adding cysteine residue to the N-terminus, was synthesized and purified by HPLC. The cysteine residue at the N-terminus of this antigen peptide was conjugated to KLH (Keyhole-limpet hemocyanin) carrier protein using MBS (m-Maleimidobenzoyl-N-hydroxysuccinimide ester). The conjugated peptide thus obtained (3 mg of the synthetic peptide plus 2 mg of the carrier protein) was dissolved in 5 mL of phosphate buffer. The emulsion obtained by mixing the conjugated peptide containing 200 µg of the synthetic peptide portion with a complete Freund's adjuvant was injected subcutaneously into a rabbit as an immune animal for the first time. Then, 14 days later, the emulsion obtained by mixing the conjugated peptide containing 100 µg of the synthetic peptide portion with an incomplete Freund's adjuvant was injected subcutaneously into the same rabbit from the second time. Likewise, four additional antigen injections were made every 14 days. Whole blood was collected on day 77 after the initial antigen injection and 20 mL of antiserum was obtained. Next, an affinity column was prepared by immobilizing the phosphorylated p62 peptide used as the antigen, and antibody that binds to the phosphorylated p62 in the antiserum was purified on the affinity column. The purified antibody was passed through an affinity column on which the non-phosphorylated p62 peptide had been immobilized. The purified antibody contained in the fractions eluted from the column was used as anti-phosphorylated p62 antibody that specifically binds the phosphorylated p62.

Specificity of the anti-phosphorylated p62 antibody thus obtained to the phosphorylated p62 protein (SEQ ID No. 1) was examined. For this purpose, Strep-tagged p62 (SEQ ID No. 1) was expressed in HEK293T cells. The Strep-p62 protein was purified from cell lysates by affinity chromatography with StrepTactin sepharose (IBA). The purified Strep-p62 protein was either treated (+) or not treated (−) with lambda protein phosphatase (Lambda PP). Both were separated by NuPAGE electrophoresis system (Invitrogen) on 12% bis-tris gel and MOPS-SDS buffer, and transferred to polyvinylidene fluoride (PVDF) membranes. p62 was detected using anti-p62 antibody (GP-62C: Progen Biotechnik) (on the left in FIG. 3; PVDF membrane) that recognizes the C-terminal domain of p62 regardless of its phosphorylation and the anti-phosphorylated p62 antibody (on the right in FIG. 3, PVDF membrane) prepared above.
==Result==
It has been revealed that the anti-phosphorylated p62 antibody generated here recognizes the phosphorylated p62 protein and does not recognize the non-phosphorylated p62 protein.
(3) Interaction Between Phosphorylated p62 and Keap1 in Cells Adenoviruses capable of expressing FLAG-tagged p62 w.t. (wild-type) (SEQ ID No. 1), FLAG-tagged S351E (SEQ ID No. 2) (pseudo-phosphorylated p62) with the substitution of glutamic acid for serine 351 of p62 of SEQ ID No. 1, FLAG-tagged S351A (SEQ ID No. 4) (non-phosphorylated p62) with the substitution of alanine for serine 351 of p62 of SEQ ID No. 1, and FLAG-tagged T352A (SEQ ID No. 6) (p62 mutant defective in interacting with Keap1) with the substitution of alanine for threonine 352 of p62 of SEQ ID No. 1, were generated using DNAs that encode wild-type p62 (p62 w.t.) (SEQ ID No. 1), mutant p62S351E (SEQ ID No. 2), mutant p62S351A (SEQ ID No. 4) and mutant p62T352A (SEQ ID No. 6), respectively, with Adenovirus expression kit (Takara Bio). Next, normal hepatocytes were cultured in 2 ml of growth medium (Williams E medium containing 10% fetal bovine serum, 5 U/mL penicillin, and 50 µg/mL streptomycin) for 24 hours. The medium was replaced with fresh medium containing the adenovirus at MOI of 50 and the culture was continued. Twenty-four hours after the replacement of the medium, whole cell extract (Total) and nuclear extract (Nucleus) were prepared. Next, immunoprecipitates were prepared from the whole cell extract with anti-FLAG antibody (Sigma Chemical). Then, the samples were separated by NuPAGE electrophoresis system (Invitrogen) on 12% bis-tris gel and MOPS-SDS buffer, and transferred to PVDF membranes. The signals were detected using anti-p62 antibody (GP62C: Progen Biotechnik), anti-Keap1 antibody (Proteintech Group), anti-phosphorylated p62 antibody, anti-Nqo1 antibody (Abcam), anti-Actin antibody (MAB1501R: Millipore), anti-Nrf2 antibody (H-300: Santa Cruz Biotechnology), and anti-LaminB antibody (M-20: Santa Cruz Biotechnology). The experiments were performed three times independently and a representative result is shown in FIG. 4.
==Result==
Intracellular Keap1 was bound to S351E (SEQ ID No. 6) rather than S351A. In addition, Nrf2 significantly accumulated in nuclei of the cells in which S351E is expressed, and expression of Nqo1 which is an Nrf2 target was induced.
(4) Effect of Phosphorylated p62 on Interaction of Nrf2 and Keap1 in Cells HEK293T cells expressing mouse Keap1 (SEQ ID No. 23) with FLAG tag attached at the N-terminus and GFP, GFP-p62, GFP-S351E (SEQ ID No. 2) or GFP-S351A (SEQ ID No. 4) were lysed in a lysis buffer to obtain cell lysate. Next, immunoprecipitation was performed using anti-FLAG antibody (Sigma Chemical) to recover the FLAG-tagged Keap1 protein and complexes interacting with Keap1. The lysates (crude) and the collected protein complexes (IP: FLAG(Keap1)) were loaded on gel by NuPAGE electrophoresis system (Invitrogen) on 12% bis-tris gel and MOPS-SDS buffer. The signals were detected using anti-FLAG antibody (Sigma Chemical), anti-GFP antibody (Invitrogen), anti-p62 antibody (GP62C: Progen Biotechnik), anti-Nrf2 antibody (H-300: Santa Cruz Biotechnology), and anti-actin antibody (MAB1501R: Chemicon International). Results are shown in FIG. 5.
==Result==
No Nrf2 was detected in the protein complexes interacting with Keap1 due to overexpression of S351E. In other words, the interaction between Nrf2 and Keap1 was disabled due to the overexpression of S351E.
==Conclusion==
As described above, phosphorylation of p62 enhances its binding affinity for Keap1 to allow p62 to be bound to Keap1. As a result, Nrf2 is released from Keap1.

Example 2

This Example shows that phosphorylation of p62 is involved in proliferation of tumor cells.
(1) Immunostaining of Human Hepatoma Cell Lines Human hepatoma (Huh-1) cells were cultured in a William's E medium containing 10% fetal bovine serum, 5 U/mL penicillin, and 50 µg/mL streptomycin.

The human hepatoma cell lines were cultured on dishes, fixed with 4% paraformaldehyde in PBS solution for 15 minutes, permeabilized with 50 µg/ml digitonin for 10 minutes and blocked with PBS containing 0.1% (vol/vol) gelatin (Sigma Chemical, #G-9391) for 30 minutes.

Next, the cells were incubated with primary antibody for 1 hour. The primary antibodies used were the anti-p62 antibody (GP62C: Progen Biotechnik), anti-Keap1 antibody (Proteintech Group) and the anti-phosphorylated p62 antibody obtained above. Double-immunostaining was performed using a combination of the anti-p62 antibody and the anti-phosphorylated p62 antibody or a combination of the anti-phosphorylated p62 antibody and the anti-Keap1 antibody. After washing, Alexa Fluor488-conjugated anti-guinea pig IgG secondary antibody (Invitrogen) or Alexa Fluor647-conjugated anti-rabbit IgG secondary antibody (Invitrogen) was added and incubated for 30 minutes. The cells were observed with the confocal laser scanning microscope (LSM510 META, Carl Zeiss) using Objective Plan-Apochromat (63 x/1.40 Oil DIC, Carl Zeiss).

==Result==
As shown in FIG. 6, in p62-positive aggregate of the human hepatoma cells, p62 were phosphorylated and Keap1 was contained.
(2) Phosphorylation of p62 and Proliferation of HCC First, p62 cDNAs which encode S349E (SEQ ID No. 8) (pseudo-phosphorylated p62) with the substitution of glutamic acid for serine 349 of human p62 (SEQ ID No. 7), S349A (SEQ ID No. 9) (non-phosphorylated p62) with the substitution of alanine for serine 349 of human p62, or T350A (SEQ ID No. 10) (p62 mutant defective in interacting with Keap1) with the substitution of alanine for threonine 350 of human p62 was prepared.

Next, a [Huh-1_p62$^{-/-}$] cell line was generated by knocking out the p62 gene in Huh-1 cells, using Zinc Finger Nuclease system (Sigma-Aldrich, CompoZr (registered trademark) Zinc Finger Nuclease). Then, adenoviruses having p62 w.t. or p62 mutant were produced, using Adenovirus expression kit (Takara Bio). The [Huh-1_p62$^{-/-}$] cells were cultured in 2 ml of a growth medium (Williams E medium containing 10% fetal bovine serum, 5 U/ml penicillin, and 50 µg/ml streptomycin) for 24 hours. The medium was replaced with a fresh medium containing adenovirus at MOI of 50 and the cells were continuously cultured. Wild-type human p62 (SEQ ID No. 7), S349E (SEQ ID No. 8), S349A (SEQ ID No. 9), and T350A (SEQ ID No. 10) were introduced into the [Huh-1_p62$^{-/-}$] cell line and thus a [Huh-1_p62$^{-/-}$_p62 w.t.] cell line with p62 w.t., a [Huh-1_p62$^{-/-}$_p62S349E] cell line with p62S349E, a [Huh-1_p62$^{-/-}$_p62S349A] cell line with p62S349A, and a [Huh-1_p62$^{-/-}$_p62T350A] cell line with p62T350A, respectively, in [Huh-1_p62$^{-/-}$] cell line was obtained.

Figure 7A:
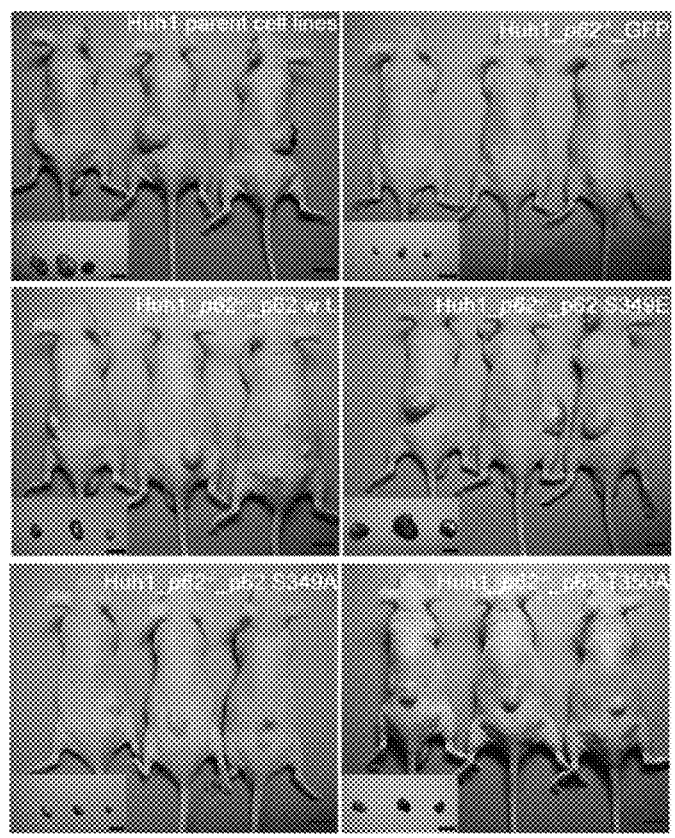

Each of the cells was transplanted subdermally into three nude mice. FIG. 7(a) shows photographs of the mice and tumors removed from these mice, taken 50 days after the transplantation of the [Huh-1] parent cell line (upper left in the figure), the [Huh-1_p62$^{-/-}$_p62w.t.] cell line (upper right in the figure), the [Huh-1_p62$^{-/-}$_p62w.t.] cell line (middle left in the figure), the [Huh-1_p62$^{-/-}$_p62S349E] cell line (middle right in the figure), the [Huh-1_p62$^{-/-}$_p62S349A] cell line (lower left in the figure), and the [Huh-1_p62$^{-/-}$_p62T350A] cell line (lower right in the figure). Each cell line was transplanted into five mice and the volume (left) and the weight (right) of the tumors were measured 50 days after the transplantation. Mean±standard error for each cell line was calculated and shown in the graphs in FIG. 7(b).

Figure 7B:
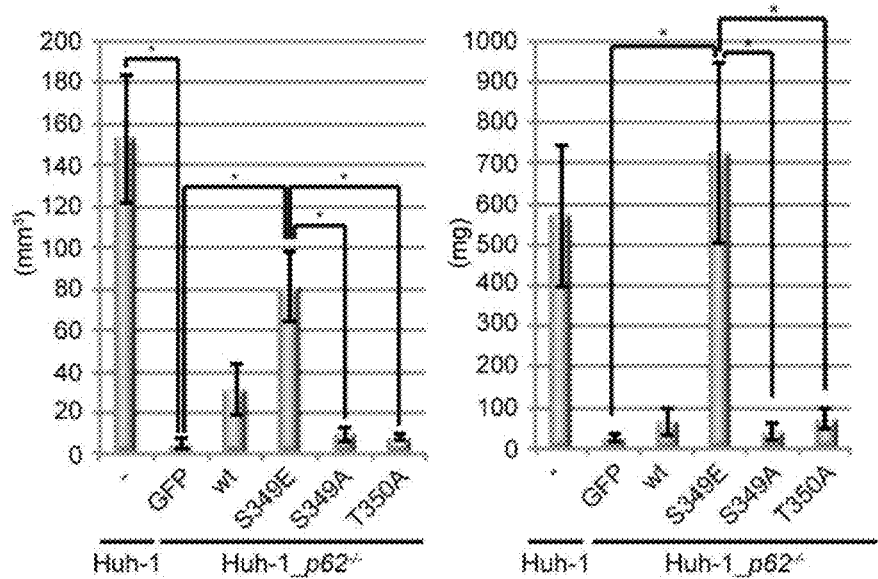

==Result==
In nude mice transplanted with the tumor cells obtained by introducing p62 (S349E) into [Huh-1_p62$^{-/-}$], in vivo proliferation of the tumor cells was significantly enhanced (p<0.05, t-study) (FIG. 7(b)).

The phosphorylation of p62 thus causes the tumor cells to be more malignant. Therefore, the use of the anti-phosphorylated p62 antibody makes it possible to diagnose the character of the tumors and to design treatment regimens and measures against the tumors.

The proliferation capacity of the tumor cells is not recovered when S349A or T350A is introduced into Huh-1_p62$^{-/-}$ (FIG. 7(b)). This suggests that antitumor agents can be obtained by screening for substances that inhibit the phosphorylation of serine at the position 351 of the amino acid sequence of SEQ ID No. 1 or a serine at a position corresponding thereto, or substances that dephosphorylate the phosphorylated serine, or substances that inhibit the binding between the phosphorylated p62 protein and Keap1.

What is claimed is:

1. A method of screening for an antitumor agent comprising: screening for a substance inhibiting the binding between an isolated phosphorylated p62 protein or a part thereof, comprising a phosphorylated serine, the serine residing in the Keap1-interacting sequence STGE (SEQ ID NO:28) of a p62 protein, and Keap1.

2. The screening method of claim 1, wherein a tumor to be treated with the antitumor agent is a liver cancer.

3. The screening method of claim 1, wherein said serine is at a position selected from a group consisting of position 260 in zebrafish p62, position 332 in pufferfish p62, position 348 in rat p62, position 349 in human, orangutan, or cattle p62, position 351 in mouse p62, position 355 in *Silurana tropicalis* p62, and position 357 in *Xenopus laevis* p62.

4. The screening method of claim 1, wherein said serine is at position 351 in a partial amino acid sequence of mouse p62 (SEQ ID NO:11).

5. The screening method of claim 1, wherein said serine is at position 348 in a partial amino acid sequence of rat p62 (SEQ ID NO:12).

6. The screening method of claim 1, wherein said serine is at position 349 in a partial amino acid sequence of human p62 (SEQ ID NO:13).

7. The screening method of claim 1, wherein said serine is at position 349 in a partial amino acid sequence of orangutan p62 (SEQ ID NO:14).

8. The screening method of claim 1, wherein said serine is at position 349 in a partial amino acid sequence of cattle p62 (SEQ ID NO:15).

9. The screening method of claim 1, wherein said serine is at position 355 in a partial amino acid sequence of *Xenopus tropicalis* p62 (SEQ ID NO:16).

10. The screening method of claim 1, wherein said serine is at position 357 in a partial amino acid sequence of *Xenopus laevis* p62 (SEQ ID NO:17).

11. The screening method of claim 1, wherein said serine is at position 332 in a partial amino acid sequence of pufferfish p62 (SEQ ID NO:18).

12. The screening method of claim 1, wherein said serine is at position 260 in a partial amino acid sequence of zebrafish p62 (SEQ ID NO:19).

* * * * *

SEQUENCE LISTING

<160> NUMBER OF SEQ ID NOS: 28

<210> SEQ ID NO 1
<211> LENGTH: 442
<212> TYPE: PRT
<213> ORGANISM: Mus musculus

<400> SEQUENCE: 1

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
            20                  25                  30

Ala Glu Ala Gln Ala Ala Gly Pro Gly Pro Cys Glu Arg Leu Leu
        35                  40                  45

Ser Arg Val Ala Val Leu Phe Pro Thr Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Glu His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Glu His Ser Lys Leu Ile Phe Pro Asn Pro Phe Gly His Leu Ser
                165                 170                 175

Asp Ser Phe Ser His Ser Arg Trp Leu Arg Lys Leu His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Asp Gly Arg Pro Cys Pro Thr Ala Glu Ser
210                 215                 220

Ala Ser Ala Pro Pro Glu Asp Pro Asn Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Thr Thr
            260                 265                 270

Pro Glu Ser Ser Ser Thr Gly Thr Glu Asp Lys Ser Asn Thr Gln Pro
        275                 280                 285

Ser Ser Cys Ser Ser Glu Val Ser Lys Pro Asp Gly Ala Gly Glu Gly
290                 295                 300

Pro Ala Gln Ser Leu Thr Glu Gln Met Lys Lys Ile Ala Leu Glu Ser
305                 310                 315                 320

Val Gly Gln Pro Glu Glu Gln Met Glu Ser Gly Asn Cys Ser Gly Gly
                325                 330                 335

Asp Asp Asp Trp Thr His Leu Ser Ser Lys Glu Val Asp Pro Ser Thr
            340                 345                 350

Gly Glu Leu Gln Ser Leu Gln Met Pro Glu Ser Glu Gly Pro Ser Ser
        355                 360                 365

```
Leu Asp Pro Ser Gln Glu Gly Pro Thr Gly Leu Lys Glu Ala Ala Leu
    370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
                405                 410                 415

Arg Leu Leu Gln Thr Lys Asn Tyr Asp Ile Gly Ala Ala Leu Asp Thr
                420                 425                 430

Ile Gln Tyr Ser Lys His Pro Pro Leu
                435                 440

<210> SEQ ID NO 2
<211> LENGTH: 442
<212> TYPE: PRT
<213> ORGANISM: Mus musculus

<400> SEQUENCE: 2

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
            20                  25                  30

Ala Glu Ala Gln Ala Ala Ala Gly Pro Gly Pro Cys Glu Arg Leu Leu
        35                  40                  45

Ser Arg Val Ala Val Leu Phe Pro Thr Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Glu His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Glu His Ser Lys Leu Ile Phe Pro Asn Pro Phe Gly His Leu Ser
                165                 170                 175

Asp Ser Phe Ser His Ser Arg Trp Leu Arg Lys Leu Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Asp Gly Arg Pro Cys Pro Thr Ala Glu Ser
210                 215                 220

Ala Ser Ala Pro Pro Glu Asp Pro Asn Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Thr Thr
            260                 265                 270

Pro Glu Ser Ser Ser Thr Gly Thr Glu Asp Lys Ser Asn Thr Gln Pro
        275                 280                 285

Ser Ser Cys Ser Ser Glu Val Ser Lys Pro Asp Gly Ala Gly Glu Gly
290                 295                 300
```

```
Pro Ala Gln Ser Leu Thr Glu Gln Met Lys Lys Ile Ala Leu Glu Ser
305                 310                 315                 320

Val Gly Gln Pro Glu Gln Met Glu Ser Gly Asn Cys Ser Gly Gly
                325                 330                 335

Asp Asp Asp Trp Thr His Leu Ser Ser Lys Glu Val Asp Pro Glu Thr
                340                 345                 350

Gly Glu Leu Gln Ser Leu Gln Met Pro Glu Ser Glu Gly Pro Ser Ser
                355                 360                 365

Leu Asp Pro Ser Gln Glu Gly Pro Thr Gly Leu Lys Glu Ala Ala Leu
    370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
                405                 410                 415

Arg Leu Leu Gln Thr Lys Asn Tyr Asp Ile Gly Ala Ala Leu Asp Thr
                420                 425                 430

Ile Gln Tyr Ser Lys His Pro Pro Leu
                435                 440

<210> SEQ ID NO 3
<211> LENGTH: 442
<212> TYPE: PRT
<213> ORGANISM: Mus musculus

<400> SEQUENCE: 3

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
                20                  25                  30

Ala Glu Ala Gln Ala Ala Gly Pro Gly Pro Cys Glu Arg Leu Leu
            35                  40                  45

Ser Arg Val Ala Val Leu Phe Pro Thr Leu Arg Pro Gly Gly Phe Gln
    50                  55                  60

Ala His Tyr Arg Asp Glu Asp Gly Asp Leu Val Ala Phe Ser Ser Asp
65              70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Glu His Arg Pro Pro
                100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Glu His Ser Lys Leu Ile Phe Pro Asn Pro Phe Gly His Leu Ser
                165                 170                 175

Asp Ser Phe Ser His Ser Arg Trp Leu Arg Lys Leu His Gly His
            180                 185                 190

Phe Gly Trp Pro Gly Trp Glu Met Gly Pro Pro Gly Asn Trp Ser Pro
                195                 200                 205

Arg Pro Pro Arg Ala Gly Asp Gly Arg Pro Cys Pro Thr Ala Glu Ser
    210                 215                 220

Ala Ser Ala Pro Pro Glu Asp Pro Asn Val Asn Phe Leu Lys Asn Val
```

```
                225                 230                 235                 240
Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Thr Thr
            260                 265                 270

Pro Glu Ser Ser Thr Gly Thr Glu Asp Lys Ser Asn Thr Gln Pro
            275                 280                 285

Ser Ser Cys Ser Ser Glu Val Ser Lys Pro Asp Gly Ala Gly Glu Gly
290                 295                 300

Pro Ala Gln Ser Leu Thr Glu Gln Met Lys Lys Ile Ala Leu Glu Ser
305                 310                 315                 320

Val Gly Gln Pro Glu Glu Gln Met Glu Ser Gly Asn Cys Ser Gly Gly
                325                 330                 335

Asp Asp Asp Trp Thr His Leu Ser Ser Lys Glu Val Pro Asp Thr
            340                 345                 350

Gly Glu Leu Gln Ser Leu Gln Met Pro Glu Ser Glu Gly Pro Ser Ser
            355                 360                 365

Leu Asp Pro Ser Gln Glu Gly Pro Thr Gly Leu Lys Glu Ala Ala Leu
370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
                405                 410                 415

Arg Leu Leu Gln Thr Lys Asn Tyr Asp Ile Gly Ala Ala Leu Asp Thr
            420                 425                 430

Ile Gln Tyr Ser Lys His Pro Pro Pro Leu
            435                 440

<210> SEQ ID NO 4
<211> LENGTH: 442
<212> TYPE: PRT
<213> ORGANISM: Mus musculus

<400> SEQUENCE: 4

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
            20                  25                  30

Ala Glu Ala Gln Ala Ala Gly Pro Gly Pro Cys Glu Arg Leu Leu
            35                  40                  45

Ser Arg Val Ala Val Leu Phe Pro Thr Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Glu His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
            130                 135                 140

Cys Pro Asp Tyr Asp Leu Cys Ser Val Cys Glu Gly Lys Gly Leu His
145                 150                 155                 160
```

```
Arg Glu His Ser Lys Leu Ile Phe Pro Asn Pro Phe Gly His Leu Ser
            165                 170                 175

Asp Ser Phe Ser His Ser Arg Trp Leu Arg Lys Leu Lys His Gly His
            180                 185                 190

Phe Gly Trp Pro Gly Trp Glu Met Gly Pro Pro Gly Asn Trp Ser Pro
            195                 200                 205

Arg Pro Pro Arg Ala Gly Asp Gly Arg Pro Cys Pro Thr Ala Glu Ser
            210                 215                 220

Ala Ser Ala Pro Pro Glu Asp Pro Asn Val Asn Phe Leu Lys Asn Val
225                 230                 235                 240

Gly Glu Ser Val Ala Ala Leu Ser Pro Leu Gly Ile Glu Val Asp
            245                 250                 255

Ile Asp Val Glu His Gly Gly Lys Arg Ser Arg Leu Thr Pro Thr Thr
            260                 265                 270

Pro Glu Ser Ser Ser Thr Gly Thr Glu Asp Lys Ser Asn Thr Gln Pro
            275                 280                 285

Ser Ser Cys Ser Ser Glu Val Ser Lys Pro Asp Gly Ala Gly Glu Gly
            290                 295                 300

Pro Ala Gln Ser Leu Thr Glu Gln Met Lys Lys Ile Ala Leu Glu Ser
305                 310                 315                 320

Val Gly Gln Pro Glu Glu Gln Met Glu Ser Gly Asn Cys Ser Gly Gly
            325                 330                 335

Asp Asp Asp Trp Thr His Leu Ser Ser Lys Glu Val Asp Pro Ala Thr
            340                 345                 350

Gly Glu Leu Gln Ser Leu Gln Met Pro Glu Ser Glu Gly Pro Ser Ser
            355                 360                 365

Leu Asp Pro Ser Gln Glu Gly Pro Thr Gly Leu Lys Glu Ala Ala Leu
            370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
            405                 410                 415

Arg Leu Leu Gln Thr Lys Asn Tyr Asp Ile Gly Ala Ala Leu Asp Thr
            420                 425                 430

Ile Gln Tyr Ser Lys His Pro Pro Leu
            435                 440

<210> SEQ ID NO 5
<211> LENGTH: 442
<212> TYPE: PRT
<213> ORGANISM: Mus musculus

<400> SEQUENCE: 5

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
            20                  25                  30

Ala Glu Ala Gln Ala Ala Gly Pro Gly Pro Cys Glu Arg Leu Leu
            35                  40                  45

Ser Arg Val Ala Val Leu Phe Pro Thr Leu Arg Pro Gly Gly Phe Gln
            50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
            85                  90                  95
```

```
Ile Tyr Ile Lys Glu Lys Lys Glu Cys Arg Arg Glu His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
            130                 135                 140

Cys Pro Asp Tyr Asp Leu Cys Ser Val Cys Glu Gly Lys Gly Leu His
145                 150                 155                 160

Arg Glu His Ser Lys Leu Ile Phe Pro Asn Pro Phe Gly His Leu Ser
                165                 170                 175

Asp Ser Phe Ser His Ser Arg Trp Leu Arg Lys Leu Lys His Gly His
            180                 185                 190

Phe Gly Trp Pro Gly Trp Glu Met Gly Pro Pro Gly Asn Trp Ser Pro
            195                 200                 205

Arg Pro Pro Arg Ala Gly Asp Gly Arg Pro Cys Pro Thr Ala Glu Ser
            210                 215                 220

Ala Ser Ala Pro Pro Glu Asp Pro Asn Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Thr Thr
            260                 265                 270

Pro Glu Ser Ser Ser Thr Gly Thr Glu Asp Lys Ser Asn Thr Gln Pro
            275                 280                 285

Ser Ser Cys Ser Ser Glu Val Ser Lys Pro Asp Gly Ala Gly Glu Gly
            290                 295                 300

Pro Ala Gln Ser Leu Thr Glu Gln Met Lys Lys Ile Ala Leu Glu Ser
305                 310                 315                 320

Val Gly Gln Pro Glu Glu Gln Met Glu Ser Gly Asn Cys Ser Gly Gly
                325                 330                 335

Asp Asp Asp Trp Thr His Leu Ser Ser Lys Glu Val Asp Pro Gly Thr
            340                 345                 350

Gly Glu Leu Gln Ser Leu Gln Met Pro Glu Ser Glu Gly Pro Ser Ser
            355                 360                 365

Leu Asp Pro Ser Gln Glu Gly Pro Thr Gly Leu Lys Glu Ala Ala Leu
            370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
                405                 410                 415

Arg Leu Leu Gln Thr Lys Asn Tyr Asp Ile Gly Ala Ala Leu Asp Thr
            420                 425                 430

Ile Gln Tyr Ser Lys His Pro Pro Leu
        435                 440

<210> SEQ ID NO 6
<211> LENGTH: 442
<212> TYPE: PRT
<213> ORGANISM: Mus musculus

<400> SEQUENCE: 6

Met Ala Ser Phe Thr Val Lys Ala Tyr Leu Leu Gly Lys Glu Glu Ala
1               5                   10                  15

Thr Arg Glu Ile Arg Arg Phe Ser Phe Cys Phe Ser Pro Glu Pro Glu
```

```
                 20                  25                  30
Ala Glu Ala Gln Ala Ala Gly Pro Gly Cys Glu Arg Leu Leu
            35                  40                  45

Ser Arg Val Ala Val Leu Phe Pro Thr Leu Arg Pro Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Glu His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
            130                 135                 140

Cys Pro Asp Tyr Asp Leu Cys Ser Val Cys Glu Gly Lys Gly Leu His
145                 150                 155                 160

Arg Glu His Ser Lys Leu Ile Phe Pro Asn Pro Phe Gly His Leu Ser
                165                 170                 175

Asp Ser Phe Ser His Ser Arg Trp Leu Arg Lys Leu Lys His Gly His
            180                 185                 190

Phe Gly Trp Pro Gly Trp Glu Met Gly Pro Pro Gly Asn Trp Ser Pro
            195                 200                 205

Arg Pro Pro Arg Ala Gly Asp Gly Arg Pro Cys Pro Thr Ala Glu Ser
    210                 215                 220

Ala Ser Ala Pro Pro Glu Asp Pro Asn Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Thr Thr
            260                 265                 270

Pro Glu Ser Ser Ser Thr Gly Thr Glu Asp Lys Ser Asn Thr Gln Pro
    275                 280                 285

Ser Ser Cys Ser Ser Glu Val Ser Lys Pro Asp Gly Ala Gly Glu Gly
    290                 295                 300

Pro Ala Gln Ser Leu Thr Glu Gln Met Lys Lys Ile Ala Leu Glu Ser
305                 310                 315                 320

Val Gly Gln Pro Glu Glu Gln Met Glu Ser Gly Asn Cys Ser Gly Gly
                325                 330                 335

Asp Asp Asp Trp Thr His Leu Ser Ser Lys Glu Val Asp Pro Ser Ala
            340                 345                 350

Gly Glu Leu Gln Ser Leu Gln Met Pro Glu Ser Glu Gly Pro Ser Ser
            355                 360                 365

Leu Asp Pro Ser Gln Glu Gly Pro Thr Gly Leu Lys Glu Ala Ala Leu
    370                 375                 380

Tyr Pro His Leu Pro Pro Glu Ala Asp Pro Arg Leu Ile Glu Ser Leu
385                 390                 395                 400

Ser Gln Met Leu Ser Met Gly Phe Ser Asp Glu Gly Gly Trp Leu Thr
                405                 410                 415

Arg Leu Leu Gln Thr Lys Asn Tyr Asp Ile Gly Ala Ala Leu Asp Thr
            420                 425                 430

Ile Gln Tyr Ser Lys His Pro Pro Leu
            435                 440
```

<210> SEQ ID NO 7
<211> LENGTH: 440
<212> TYPE: PRT
<213> ORGANISM: Homo sapiens

<400> SEQUENCE: 7

```
Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
        115                 120                 125

Asp Gly Cys Asn Gly Pro Val Val Gly Thr Arg Tyr Lys Cys Ser Val
    130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
            180                 185                 190

Phe Gly Trp Pro Gly Trp Glu Met Gly Pro Pro Gly Asn Trp Ser Pro
        195                 200                 205

Arg Pro Pro Arg Ala Gly Glu Ala Arg Pro Gly Pro Thr Ala Glu Ser
    210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
        275                 280                 285

Cys Cys Ser Asp Pro Ser Lys Pro Gly Gly Asn Val Glu Gly Ala Thr
    290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
        355                 360                 365

Pro Ser Gln Glu Gly Pro Thr Gly Leu Lys Glu Ala Ala Leu Tyr Pro
```

```
                   370                 375                 380
His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
                405                 410                 415

Leu Gln Thr Lys Asn Tyr Asp Ile Gly Ala Ala Leu Asp Thr Ile Gln
                420                 425                 430

Tyr Ser Lys His Pro Pro Leu
                435                 440

<210> SEQ ID NO 8
<211> LENGTH: 440
<212> TYPE: PRT
<213> ORGANISM: Homo sapiens

<400> SEQUENCE: 8

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
                20                  25                  30

Ala Glu Ala Glu Ala Ala Gly Pro Gly Pro Cys Glu Arg Leu Leu
                35                  40                  45

Ser Arg Val Ala Ala Leu Phe Pro Ala Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
                100                 105                 110

Cys Ala Gln Glu Ala Pro Arg Asn Met Val His Pro Asn Val Ile Cys
                115                 120                 125

Asp Gly Cys Asn Gly Pro Val Val Gly Thr Arg Tyr Lys Cys Ser Val
                130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
                180                 185                 190

Phe Gly Trp Pro Gly Trp Glu Met Gly Pro Pro Gly Asn Trp Ser Pro
                195                 200                 205

Arg Pro Pro Arg Ala Gly Glu Ala Arg Pro Gly Pro Thr Ala Glu Ser
                210                 215                 220

Ala Ser Gly Pro Ser Glu Asp Pro Ser Val Asn Phe Leu Lys Asn Val
225                 230                 235                 240

Gly Glu Ser Val Ala Ala Leu Ser Pro Leu Gly Ile Glu Val Asp
                245                 250                 255

Ile Asp Val Glu His Gly Gly Lys Arg Ser Arg Leu Thr Pro Val Ser
                260                 265                 270

Pro Glu Ser Ser Ser Thr Glu Glu Lys Ser Ser Gln Pro Ser Ser
                275                 280                 285

Cys Cys Ser Asp Pro Ser Lys Pro Gly Gly Asn Val Glu Gly Ala Thr
                290                 295                 300
```

-continued

```
Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
            325                 330                 335

Asp Trp Thr His Leu Ser Ser Lys Glu Val Asp Pro Glu Thr Gly Glu
            340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
            370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
            405                 410                 415

Leu Gln Thr Lys Asn Tyr Asp Ile Gly Ala Ala Leu Asp Thr Ile Gln
            420                 425                 430

Tyr Ser Lys His Pro Pro Leu
            435                 440

<210> SEQ ID NO 9
<211> LENGTH: 440
<212> TYPE: PRT
<213> ORGANISM: Homo sapiens

<400> SEQUENCE: 9

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
            35                  40                  45

Ser Arg Val Ala Ala Leu Phe Pro Ala Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
            85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
            165                 170                 175

Glu Gly Phe Ser His Ser Arg Trp Leu Arg Lys Val Lys His Gly His
            180                 185                 190

Phe Gly Trp Pro Gly Trp Glu Met Gly Pro Gly Asn Trp Ser Pro
            195                 200                 205

Arg Pro Pro Arg Ala Gly Glu Ala Arg Pro Gly Pro Thr Ala Glu Ser
            210                 215                 220

Ala Ser Gly Pro Ser Glu Asp Pro Ser Val Asn Phe Leu Lys Asn Val
225                 230                 235                 240
```

-continued

Gly Glu Ser Val Ala Ala Ala Leu Ser Pro Leu Gly Ile Glu Val Asp
            245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
            275                 280                 285

Cys Cys Ser Asp Pro Ser Lys Pro Gly Gly Asn Val Glu Gly Ala Thr
            290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
            325                 330                 335

Asp Trp Thr His Leu Ser Ser Lys Glu Val Asp Pro Ala Thr Gly Glu
            340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
            370                 375                 380

His Leu Pro Pro Glu Ala Asp Pro Arg Leu Ile Glu Ser Leu Ser Gln
385                 390                 395                 400

Met Leu Ser Met Gly Phe Ser Asp Glu Gly Gly Trp Leu Thr Arg Leu
            405                 410                 415

Leu Gln Thr Lys Asn Tyr Asp Ile Gly Ala Ala Leu Asp Thr Ile Gln
            420                 425                 430

Tyr Ser Lys His Pro Pro Leu
            435                 440

<210> SEQ ID NO 10
<211> LENGTH: 440
<212> TYPE: PRT
<213> ORGANISM: Homo sapiens

<400> SEQUENCE: 10

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
            35                  40                  45

Ser Arg Val Ala Ala Leu Phe Pro Ala Leu Arg Pro Gly Gly Phe Gln
50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
            85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
            130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser

```
                    165                 170                 175
Glu Gly Phe Ser His Ser Arg Trp Leu Arg Lys Val Lys His Gly His
            180                 185                 190
Phe Gly Trp Pro Gly Trp Glu Met Gly Pro Pro Gly Asn Trp Ser Pro
            195                 200                 205
Arg Pro Pro Arg Ala Gly Glu Ala Arg Pro Gly Pro Thr Ala Glu Ser
210                 215                 220
Ala Ser Gly Pro Ser Glu Asp Pro Ser Val Asn Phe Leu Lys Asn Val
225                 230                 235                 240
Gly Glu Ser Val Ala Ala Leu Ser Pro Leu Gly Ile Glu Val Asp
                245                 250                 255
Ile Asp Val Glu His Gly Gly Lys Arg Ser Arg Leu Thr Pro Val Ser
            260                 265                 270
Pro Glu Ser Ser Thr Glu Glu Lys Ser Ser Gln Pro Ser Ser
            275                 280                 285
Cys Cys Ser Asp Pro Ser Lys Pro Gly Gly Asn Val Glu Gly Ala Thr
290                 295                 300
Gln Ser Leu Ala Glu Gln Met Arg Lys Ile Ala Leu Glu Ser Glu Gly
305                 310                 315                 320
Arg Pro Glu Glu Gln Met Glu Ser Asp Asn Cys Ser Gly Asp Asp
                325                 330                 335
Asp Trp Thr His Leu Ser Ser Lys Glu Val Asp Pro Ser Ala Gly Glu
            340                 345                 350
Leu Gln Ser Leu Gln Met Pro Glu Ser Glu Gly Pro Ser Ser Leu Asp
            355                 360                 365
Pro Ser Gln Glu Gly Pro Thr Gly Leu Lys Glu Ala Ala Leu Tyr Pro
370                 375                 380
His Leu Pro Pro Glu Ala Asp Pro Arg Leu Ile Glu Ser Leu Ser Gln
385                 390                 395                 400
Met Leu Ser Met Gly Phe Ser Asp Glu Gly Gly Trp Leu Thr Arg Leu
                405                 410                 415
Leu Gln Thr Lys Asn Tyr Asp Ile Gly Ala Ala Leu Asp Thr Ile Gln
            420                 425                 430
Tyr Ser Lys His Pro Pro Leu
            435                 440

<210> SEQ ID NO 11
<211> LENGTH: 42
<212> TYPE: PRT
<213> ORGANISM: Mus musculus

<400> SEQUENCE: 11

Ser Gly Gly Asp Asp Asp Trp Thr His Leu Ser Ser Lys Glu Val Asp
1               5                   10                  15
Pro Ser Thr Gly Glu Leu Gln Ser Leu Gln Met Pro Glu Ser Glu Gly
            20                  25                  30
Pro Ser Ser Leu Asp Pro Ser Gln Glu Gly
        35                  40

<210> SEQ ID NO 12
<211> LENGTH: 42
<212> TYPE: PRT
<213> ORGANISM: Rattus norvegicus

<400> SEQUENCE: 12

Ser Gly Gly Asp Asp Asp Trp Thr His Leu Ser Ser Lys Glu Val Asp
```

```
                1               5                  10                 15
Pro Ser Thr Gly Glu Leu Gln Ser Leu Gln Met Pro Glu Ser Glu Gly
                20                 25                 30

Pro Ser Ser Leu Asp Pro Ser Gln Glu Gly
        35                40

<210> SEQ ID NO 13
<211> LENGTH: 42
<212> TYPE: PRT
<213> ORGANISM: Homo sapiens

<400> SEQUENCE: 13

Ser Gly Gly Asp Asp Asp Trp Thr His Leu Ser Ser Lys Glu Val Asp
1               5                   10                  15

Pro Ser Thr Gly Glu Leu Gln Ser Leu Gln Met Pro Glu Ser Glu Gly
                20                  25                  30

Pro Ser Ser Leu Asp Pro Ser Gln Glu Gly
        35                  40

<210> SEQ ID NO 14
<211> LENGTH: 42
<212> TYPE: PRT
<213> ORGANISM: Pongo pygmaeus

<400> SEQUENCE: 14

Ser Gly Gly Asp Asp Asp Trp Thr His Leu Ser Ser Lys Glu Val Asp
1               5                   10                  15

Pro Ser Thr Gly Glu Leu Gln Ser Leu Gln Met Pro Glu Ser Glu Gly
                20                  25                  30

Pro Ser Ser Leu Asp Pro Ser Gln Glu Gly
        35                  40

<210> SEQ ID NO 15
<211> LENGTH: 42
<212> TYPE: PRT
<213> ORGANISM: Bos taurus

<400> SEQUENCE: 15

Ser Gly Gly Asp Asp Asp Trp Thr His Leu Ser Ser Lys Glu Val Asp
1               5                   10                  15

Pro Ser Thr Gly Glu Leu Gln Ser Leu Gln Met Pro Glu Ser Glu Gly
                20                  25                  30

Pro Ser Ser Leu Asp Pro Ser Gln Glu Gly
        35                  40

<210> SEQ ID NO 16
<211> LENGTH: 42
<212> TYPE: PRT
<213> ORGANISM: Xenopus tropicalis

<400> SEQUENCE: 16

Ser Gly Gly Asp Asp Asp Trp Thr His Val Ser Ser Lys Glu Val Asp
1               5                   10                  15

Pro Ser Thr Gly Glu Leu Gln Ser Leu Gln Leu Met Glu Thr Gly Gln
                20                  25                  30

Pro Cys Ser Leu Asp Pro Thr Arg Ser Ser
        35                  40

<210> SEQ ID NO 17
<211> LENGTH: 42
```

```
<212> TYPE: PRT
<213> ORGANISM: Xenopus laevis

<400> SEQUENCE: 17

Ala Val Gly Asp Asp Trp Thr His Val Ser Ser Lys Glu Val Asp
1               5                   10                  15

Pro Ser Thr Gly Glu Leu Gln Ser Leu Gln Leu Ile Glu Thr Gly Gln
                20                  25                  30

Pro Cys Ser Leu Asp Pro Asn Arg Ser Ser
            35                  40

<210> SEQ ID NO 18
<211> LENGTH: 31
<212> TYPE: PRT
<213> ORGANISM: Puffer

<400> SEQUENCE: 18

Ser Asp Glu Glu Trp Thr His Leu Ser Pro Lys Glu Val Asp Pro Ser
1               5                   10                  15

Thr Gly Glu Leu Gln Ser Leu Gln Asn Gln Gly Leu Pro Ser Gly
                20                  25                  30

<210> SEQ ID NO 19
<211> LENGTH: 40
<212> TYPE: PRT
<213> ORGANISM: Danio rerio

<400> SEQUENCE: 19

Ser Asp Glu Glu Trp Thr His Leu Ser Ala Lys Glu Val Asp Pro Ser
1               5                   10                  15

Thr Gly Glu Leu Gln Ser Leu Arg Leu Glu Gln Asp Gly Ala Asp Leu
                20                  25                  30

Pro Ala Pro Leu Asn Thr Ala Ser
            35                  40

<210> SEQ ID NO 20
<211> LENGTH: 14
<212> TYPE: PRT
<213> ORGANISM: Mus musculus

<400> SEQUENCE: 20

Lys Glu Val Asp Pro Ser Thr Gly Glu Leu Gln Ser Leu Gln
1               5                   10

<210> SEQ ID NO 21
<211> LENGTH: 9
<212> TYPE: PRT
<213> ORGANISM: Mus musculus

<400> SEQUENCE: 21

Val Asp Pro Ser Thr Gly Glu Leu Gln
1               5

<210> SEQ ID NO 22
<211> LENGTH: 14
<212> TYPE: PRT
<213> ORGANISM: Mus musculus

<400> SEQUENCE: 22

Cys Lys Glu Val Asp Pro Ser Thr Gly Glu Leu Gln Ser Leu
1               5                   10
```

<210> SEQ ID NO 23
<211> LENGTH: 624
<212> TYPE: PRT
<213> ORGANISM: Mus musculus

<400> SEQUENCE: 23

```
Met Gln Pro Glu Pro Lys Leu Ser Gly Ala Pro Arg Ser Ser Gln Phe
1               5                   10                  15

Leu Pro Leu Trp Ser Lys Cys Pro Glu Gly Ala Gly Asp Ala Val Met
            20                  25                  30

Tyr Ala Ser Thr Glu Cys Lys Ala Glu Val Thr Pro Ser Gln Asp Gly
        35                  40                  45

Asn Arg Thr Phe Ser Tyr Thr Leu Glu Asp His Thr Lys Gln Ala Phe
    50                  55                  60

Gly Val Met Asn Glu Leu Arg Leu Ser Gln Gln Leu Cys Asp Val Thr
65                  70                  75                  80

Leu Gln Val Lys Tyr Glu Asp Ile Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Val Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Thr Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220

His Cys Gln Leu Ala Thr Leu Ile Ser Arg Asp Asp Leu Asn Val Arg
225                 230                 235                 240

Cys Glu Ser Glu Val Phe His Ala Cys Ile Asp Trp Val Lys Tyr Asp
                245                 250                 255

Cys Pro Gln Arg Arg Phe Tyr Val Gln Ala Leu Leu Arg Ala Val Arg
            260                 265                 270

Cys His Ala Leu Thr Pro Arg Phe Leu Gln Thr Gln Leu Gln Lys Cys
        275                 280                 285

Glu Ile Leu Gln Ala Asp Ala Arg Cys Lys Asp Tyr Leu Val Gln Ile
    290                 295                 300

Phe Gln Glu Leu Thr Leu His Lys Pro Thr Gln Ala Val Pro Cys Arg
305                 310                 315                 320

Ala Pro Lys Val Gly Arg Leu Ile Tyr Thr Ala Gly Gly Tyr Phe Arg
                325                 330                 335

Gln Ser Leu Ser Tyr Leu Glu Ala Tyr Asn Pro Ser Asn Gly Ser Trp
            340                 345                 350

Leu Arg Leu Ala Asp Leu Gln Val Pro Arg Ser Gly Leu Ala Gly Cys
        355                 360                 365

Val Val Gly Gly Leu Leu Tyr Ala Val Gly Gly Arg Asn Asn Ser Pro
    370                 375                 380
```

```
Asp Gly Asn Thr Asp Ser Ser Ala Leu Asp Cys Tyr Asn Pro Met Thr
385                 390                 395                 400

Asn Gln Trp Ser Pro Cys Ala Ser Met Ser Val Pro Arg Asn Arg Ile
            405                 410                 415

Gly Val Gly Val Ile Asp Gly His Ile Tyr Ala Val Gly Gly Ser His
        420                 425                 430

Gly Cys Ile His His Ser Ser Val Glu Arg Tyr Glu Pro Glu Arg Asp
    435                 440                 445

Glu Trp His Leu Val Ala Pro Met Leu Thr Arg Arg Ile Gly Val Gly
450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
            485                 490                 495

Trp Arg Met Ile Thr Pro Met Asn Thr Ile Arg Ser Gly Ala Gly Val
        500                 505                 510

Cys Val Leu His Asn Cys Ile Tyr Ala Ala Gly Gly Tyr Asp Gly Gln
    515                 520                 525

Asp Gln Leu Asn Ser Val Glu Arg Tyr Asp Val Glu Thr Glu Thr Trp
530                 535                 540

Thr Phe Val Ala Pro Met Arg His His Arg Ser Ala Leu Gly Ile Thr
545                 550                 555                 560

Val His Gln Gly Lys Ile Tyr Val Leu Gly Gly Tyr Asp Gly His Thr
            565                 570                 575

Phe Leu Asp Ser Val Glu Cys Tyr Asp Pro Asp Ser Asp Thr Trp Ser
        580                 585                 590

Glu Val Thr Arg Met Thr Ser Gly Arg Ser Gly Val Gly Val Ala Val
    595                 600                 605

Thr Met Glu Pro Cys Arg Lys Gln Ile Asp Gln Gln Asn Cys Thr Cys
610                 615                 620

<210> SEQ ID NO 24
<211> LENGTH: 289
<212> TYPE: PRT
<213> ORGANISM: Mus musculus

<400> SEQUENCE: 24

Ala Pro Lys Val Gly Arg Leu Ile Tyr Thr Ala Gly Gly Tyr Phe Arg
1               5                   10                  15

Gln Ser Leu Ser Tyr Leu Glu Ala Tyr Asn Pro Ser Asn Gly Ser Trp
            20                  25                  30

Leu Arg Leu Ala Asp Leu Gln Val Pro Arg Ser Gly Leu Ala Gly Cys
        35                  40                  45

Val Val Gly Gly Leu Leu Tyr Ala Val Gly Gly Arg Asn Asn Ser Pro
    50                  55                  60

Asp Gly Asn Thr Asp Ser Ser Ala Leu Asp Cys Tyr Asn Pro Met Thr
65                  70                  75                  80

Asn Gln Trp Ser Pro Cys Ala Ser Met Ser Val Pro Arg Asn Arg Ile
            85                  90                  95

Gly Val Gly Val Ile Asp Gly His Ile Tyr Ala Val Gly Gly Ser His
        100                 105                 110

Gly Cys Ile His His Ser Ser Val Glu Arg Tyr Glu Pro Glu Arg Asp
    115                 120                 125

Glu Trp His Leu Val Ala Pro Met Leu Thr Arg Arg Ile Gly Val Gly
130                 135                 140
```

```
Val Ala Val Leu Asn Arg Leu Leu Tyr Ala Val Gly Gly Phe Asp Gly
145                 150                 155                 160

Thr Asn Arg Leu Asn Ser Ala Glu Cys Tyr Tyr Pro Glu Arg Asn Glu
                165                 170                 175

Trp Arg Met Ile Thr Pro Met Asn Thr Ile Arg Ser Gly Ala Gly Val
            180                 185                 190

Cys Val Leu His Asn Cys Ile Tyr Ala Ala Gly Gly Tyr Asp Gly Gln
            195                 200                 205

Asp Gln Leu Asn Ser Val Glu Arg Tyr Asp Val Glu Thr Glu Thr Trp
        210                 215                 220

Thr Phe Val Ala Pro Met Arg His His Arg Ser Ala Leu Gly Ile Thr
225                 230                 235                 240

Val His Gln Gly Lys Ile Tyr Val Leu Gly Gly Tyr Asp Gly His Thr
                245                 250                 255

Phe Leu Asp Ser Val Glu Cys Tyr Asp Pro Asp Ser Asp Thr Trp Ser
            260                 265                 270

Glu Val Thr Arg Met Thr Ser Gly Arg Ser Gly Val Gly Val Ala Val
            275                 280                 285

Thr
```

```
<210> SEQ ID NO 25
<211> LENGTH: 624
<212> TYPE: PRT
<213> ORGANISM: Homo sapiens

<400> SEQUENCE: 25
```

```
Met Gln Pro Asp Pro Arg Pro Ser Gly Ala Gly Ala Cys Cys Arg Phe
1               5                   10                  15

Leu Pro Leu Gln Ser Gln Cys Pro Glu Gly Ala Gly Asp Ala Val Met
            20                  25                  30

Tyr Ala Ser Thr Glu Cys Lys Ala Glu Val Thr Pro Ser Gln His Gly
        35                  40                  45

Asn Arg Thr Phe Ser Tyr Thr Leu Glu Asp His Thr Lys Gln Ala Phe
    50                  55                  60

Gly Ile Met Asn Glu Leu Arg Leu Ser Gln Gln Leu Cys Asp Val Thr
65                  70                  75                  80

Leu Gln Val Lys Tyr Gln Asp Ala Pro Ala Ala Gln Phe Met Ala His
                85                  90                  95

Lys Val Val Leu Ala Ser Ser Ser Pro Val Phe Lys Ala Met Phe Thr
            100                 105                 110

Asn Gly Leu Arg Glu Gln Gly Met Glu Val Val Ser Ile Glu Gly Ile
        115                 120                 125

His Pro Lys Val Met Glu Arg Leu Ile Glu Phe Ala Tyr Thr Ala Ser
    130                 135                 140

Ile Ser Met Gly Glu Lys Cys Val Leu His Val Met Asn Gly Ala Val
145                 150                 155                 160

Met Tyr Gln Ile Asp Ser Val Val Arg Ala Cys Ser Asp Phe Leu Val
                165                 170                 175

Gln Gln Leu Asp Pro Ser Asn Ala Ile Gly Ile Ala Asn Phe Ala Glu
            180                 185                 190

Gln Ile Gly Cys Val Glu Leu His Gln Arg Ala Arg Glu Tyr Ile Tyr
        195                 200                 205

Met His Phe Gly Glu Val Ala Lys Gln Glu Glu Phe Phe Asn Leu Ser
    210                 215                 220
```

His Cys Gln Leu Val Thr Leu Ile Ser Arg Asp Asp Leu Asn Val Arg
225                 230                 235                 240

Cys Glu Ser Glu Val Phe His Ala Cys Ile Asn Trp Val Lys Tyr Asp
            245                 250                 255

Cys Glu Gln Arg Arg Phe Tyr Val Gln Ala Leu Leu Arg Ala Val Arg
        260                 265                 270

Cys His Ser Leu Thr Pro Asn Phe Leu Gln Met Gln Leu Gln Lys Cys
    275                 280                 285

Glu Ile Leu Gln Ser Asp Ser Arg Cys Lys Asp Tyr Leu Val Lys Ile
290                 295                 300

Phe Glu Glu Leu Thr Leu His Lys Pro Thr Gln Val Met Pro Cys Arg
305                 310                 315                 320

Ala Pro Lys Val Gly Arg Leu Ile Tyr Thr Ala Gly Gly Tyr Phe Arg
            325                 330                 335

Gln Ser Leu Ser Tyr Leu Glu Ala Tyr Asn Pro Ser Asp Gly Thr Trp
        340                 345                 350

Leu Arg Leu Ala Asp Leu Gln Val Pro Arg Ser Gly Leu Ala Gly Cys
    355                 360                 365

Val Val Gly Gly Leu Leu Tyr Ala Val Gly Gly Arg Asn Asn Ser Pro
370                 375                 380

Asp Gly Asn Thr Asp Ser Ser Ala Leu Asp Cys Tyr Asn Pro Met Thr
385                 390                 395                 400

Asn Gln Trp Ser Pro Cys Ala Pro Met Ser Val Pro Arg Asn Arg Ile
            405                 410                 415

Gly Val Gly Val Ile Asp Gly His Ile Tyr Ala Val Gly Gly Ser His
        420                 425                 430

Gly Cys Ile His His Asn Ser Val Glu Arg Tyr Glu Pro Glu Arg Asp
    435                 440                 445

Glu Trp His Leu Val Ala Pro Met Leu Thr Arg Arg Ile Gly Val Gly
450                 455                 460

Val Ala Val Leu Asn Arg Leu Leu Tyr Ala Val Gly Gly Phe Asp Gly
465                 470                 475                 480

Thr Asn Arg Leu Asn Ser Ala Glu Cys Tyr Tyr Pro Glu Arg Asn Glu
            485                 490                 495

Trp Arg Met Ile Thr Ala Met Asn Thr Ile Arg Ser Gly Ala Gly Val
        500                 505                 510

Cys Val Leu His Asn Cys Ile Tyr Ala Ala Gly Gly Tyr Asp Gly Gln
    515                 520                 525

Asp Gln Leu Asn Ser Val Glu Arg Tyr Asp Val Glu Thr Glu Thr Trp
530                 535                 540

Thr Phe Val Ala Pro Met Lys His Arg Arg Ser Ala Leu Gly Ile Thr
545                 550                 555                 560

Val His Gln Gly Arg Ile Tyr Val Leu Gly Gly Tyr Asp Gly His Thr
            565                 570                 575

Phe Leu Asp Ser Val Glu Cys Tyr Asp Pro Asp Thr Asp Thr Trp Ser
        580                 585                 590

Glu Val Thr Arg Met Thr Ser Gly Arg Ser Gly Val Gly Val Ala Val
    595                 600                 605

Thr Met Glu Pro Cys Arg Lys Gln Ile Asp Gln Gln Asn Cys Thr Cys
610                 615                 620

<210> SEQ ID NO 26
<211> LENGTH: 9

```
<212> TYPE: PRT
<213> ORGANISM: Mus musculus

<400> SEQUENCE: 26

Leu Asp Glu Glu Thr Gly Glu Phe Leu
1               5

<210> SEQ ID NO 27
<211> LENGTH: 316
<212> TYPE: PRT
<213> ORGANISM: Mus musculus

<400> SEQUENCE: 27

Thr Leu His Lys Pro Thr Gln Ala Val Pro Cys Arg Ala Pro Lys Val
1               5                   10                  15

Gly Arg Leu Ile Tyr Thr Ala Gly Gly Tyr Phe Arg Gln Ser Leu Ser
                20                  25                  30

Tyr Leu Glu Ala Tyr Asn Pro Ser Asn Gly Ser Trp Leu Arg Leu Ala
            35                  40                  45

Asp Leu Gln Val Pro Arg Ser Gly Leu Ala Gly Cys Val Val Gly Gly
        50                  55                  60

Leu Leu Tyr Ala Val Gly Gly Arg Asn Asn Ser Pro Asp Gly Asn Thr
65                  70                  75                  80

Asp Ser Ser Ala Leu Asp Cys Tyr Asn Pro Met Thr Asn Gln Trp Ser
                85                  90                  95

Pro Cys Ala Ser Met Ser Val Pro Arg Asn Arg Ile Gly Val Gly Val
            100                 105                 110

Ile Asp Gly His Ile Tyr Ala Val Gly Gly Ser His Gly Cys Ile His
        115                 120                 125

His Ser Ser Val Glu Arg Tyr Glu Pro Glu Arg Asp Glu Trp His Leu
130                 135                 140

Val Ala Pro Met Leu Thr Arg Arg Ile Gly Val Gly Val Ala Val Leu
145                 150                 155                 160

Asn Arg Leu Leu Tyr Ala Val Gly Gly Phe Asp Gly Thr Asn Arg Leu
                165                 170                 175

Asn Ser Ala Glu Cys Tyr Tyr Pro Glu Arg Asn Glu Trp Arg Met Ile
            180                 185                 190

Thr Pro Met Asn Thr Ile Arg Ser Gly Ala Gly Val Cys Val Leu His
        195                 200                 205

Asn Cys Ile Tyr Ala Ala Gly Gly Tyr Asp Gly Gln Asp Gln Leu Asn
    210                 215                 220

Ser Val Glu Arg Tyr Asp Val Glu Thr Glu Thr Trp Thr Phe Val Ala
225                 230                 235                 240

Pro Met Arg His His Arg Ser Ala Leu Gly Ile Thr Val His Gln Gly
                245                 250                 255

Lys Ile Tyr Val Leu Gly Gly Tyr Asp Gly His Thr Phe Leu Asp Ser
            260                 265                 270

Val Glu Cys Tyr Asp Pro Asp Ser Asp Thr Trp Ser Glu Val Thr Arg
        275                 280                 285

Met Thr Ser Gly Arg Ser Gly Val Gly Val Ala Val Thr Met Glu Pro
    290                 295                 300

Cys Arg Lys Gln Ile Asp Gln Gln Asn Cys Thr Cys
305                 310                 315

<210> SEQ ID NO 28
<211> LENGTH: 4
```

```
<212> TYPE: PRT
<213> ORGANISM: Mus musculus

<400> SEQUENCE: 28

Ser Thr Gly Glu
1
```